United States Patent [19]

Fuller et al.

[11] Patent Number: 5,174,963
[45] Date of Patent: Dec. 29, 1992

[54] BLOOD GLUCOSE REFLECTANCE METER INCLUDING A NULL PROMPTING MEANS AND A DEVICE FOR PROVIDING A CONSTANT BRIGHTNESS LIGHT

[75] Inventors: Maurice D. Fuller; Richard A. Riedel, both of Carmel, Ind.

[73] Assignee: United Medical Manufacturing Company, Indianapolis, Ind.

[21] Appl. No.: 638,170

[22] Filed: Jan. 7, 1991

[51] Int. Cl.$^5$ ............................................. G01N 21/77
[52] U.S. Cl. .............................. 422/82.05; 250/238; 356/446; 422/82.12; 422/56; 436/95; 436/169
[58] Field of Search ...................... 422/56, 68.1, 82.01, 422/82.02, 82.05, 82.12; 436/95, 169; 356/446; 250/238

[56] References Cited

U.S. PATENT DOCUMENTS

| | | | |
|---|---|---|---|
| 3,907,503 | 9/1975 | Betts et al. | 356/446 X |
| 4,797,256 | 1/1989 | Watlington | 422/56 X |
| 4,871,258 | 10/1989 | Herpichboehm et al. | 356/423 X |
| 4,895,444 | 1/1990 | Miyata et al. | 356/128 |
| 4,917,500 | 4/1990 | Lugos | 356/406 |
| 5,029,277 | 7/1991 | Kane | 250/238 X |
| 5,057,275 | 10/1991 | Neuman | 422/68.1 X |

FOREIGN PATENT DOCUMENTS 3026439  2/1982  Fed. Rep. of Germany ...... 356/446

Primary Examiner—Robert J. Hill, Jr.
Attorney, Agent, or Firm—Woodard, Emhardt, Naughton, Moriarty & McNett

[57] ABSTRACT

A portable blood glucose monitoring meter that employs an analog circuit in conjunction with a manually rotatable dial that varies the resistance of a potentiometer to locate a null position that balances the measure taken of the blood glucose-induced changes in the chemistries of disposable test strips. The dial supports a replaceable, pre-printed, man-readable calibration disk. The calibration disk displays in man-readable format blood glucose concentrations in milligrams per milliliter calibrated to the specific batch-lot chemistries of the disposable test strips used with the meter. A patient places a replaceable batch-lot calibration disk upon the dial, and inserts a corresponding test strip bearing a drop of capillary blood into the meter. The patient then manually adjusts the dial until prompting arrows indicate a null position. If the dial has rotated past the null position, an opposing arrow will illuminate indicating a need to rotate the dial in the opposite direction. The procedure is repeated until a null position is found. At the null position, the prompting arrows illuminate simultaneously. The concentration of the patient's blood glucose in milligrams per milliliter is then read directly from the number appearing on the calibration disk at the null point.

14 Claims, 3 Drawing Sheets

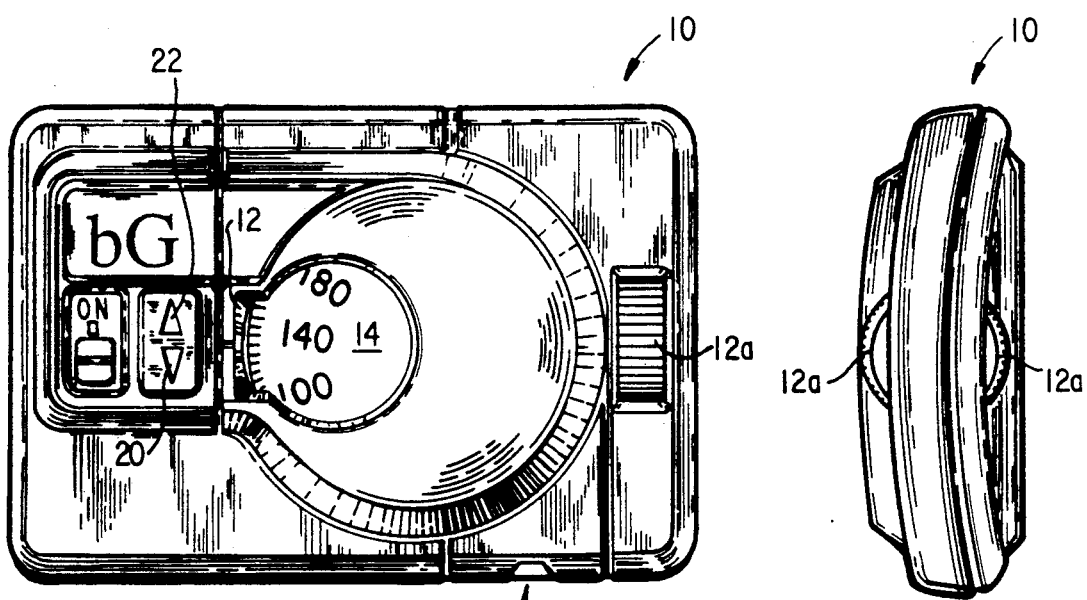
Fig.1  Fig.2
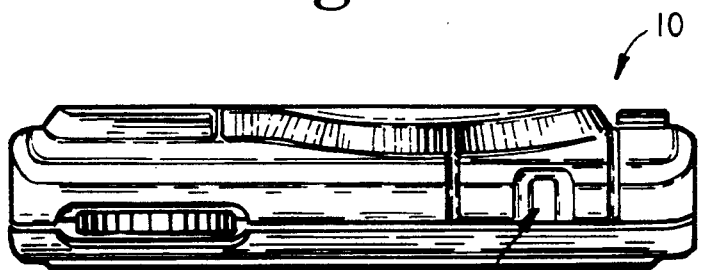
Fig.3
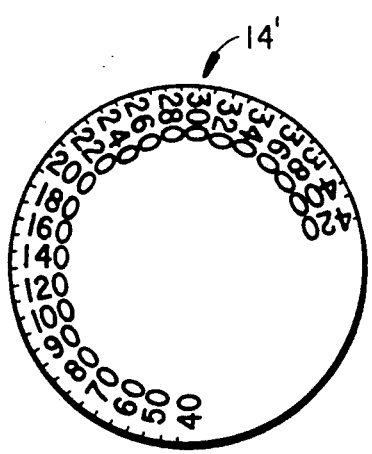 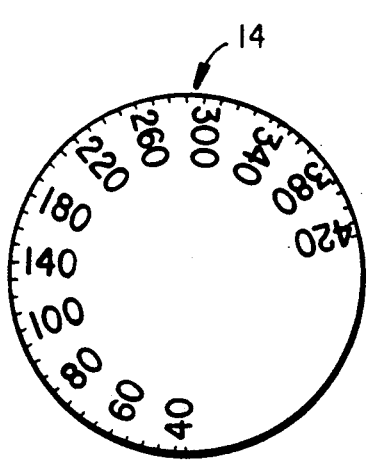
Fig.5  Fig.4

BLOOD GLUCOSE REFLECTANCE METER INCLUDING A NULL PROMPTING MEANS AND A DEVICE FOR PROVIDING A CONSTANT BRIGHTNESS LIGHT

The invention relates generally to blood glucose monitoring, and more specifically to portable blood glucose monitoring meters.

BACKGROUND OF THE INVENTION

Portable blood glucose monitoring meters were first made available for use in the late 1970's. Portable meters provided patients and health care providers with the means to improve insulin control by permitting them to determine blood glucose levels quickly and with reasonable accuracy, without the need for vein puncture and laboratory analysis. Since the introduction of such meters, improvements to date have produced portable meters offering greater convenience in smaller sizes with more features.

Portable blood glucose monitoring meters today typically utilize disposable test strips, similar to litmus paper, that have applied chemistries that either produce a color change or a change in electrical resistance when a drop of a patient's capillary blood is applied to the chemistry. In the case of test strips with chemistries that produce a color change, the strip becomes darker in proportion to the amount of blood glucose present in the blood. In such cases, the strip bearing the patient's blood is inserted into the meter and the color change in the chemistry on the strip is measured using an optical reflectance system within the meter. A microprocessor-based program within the meter then processes the color change measurement and generates a digital readout of the corresponding concentration in milligrams per milliliter of blood glucose in the patient's capillary blood Such meters are commonly known as reflectance meters, and they are the most common type of portable blood glucose monitoring meter in use today.

In the case of test strips with applied chemistries that change in electrical resistance when a drop of a patient's capillary blood is applied to the strip, the change in electrical resistance is proportional to the concentration of blood glucose in the blood. In such cases, the strip is inserted into the meter and the change in electrical resistance is measured by the meter. A microprocessor-based program within the meter then processes the electrical resistance measurement and generates a digital readout of the corresponding concentration in milligrams per milliliter of blood glucose in the patient's capillary blood. Such meters are the least common type of portable blood glucose monitoring meters in use today.

In addition to generating digital readouts of blood glucose concentrations, another key function of the microprocessors found in all portable blood glucose monitoring meters in use today is the application of empirically derived correction factors to account for slight variations in the chemistries applied to test strips at the time of manufacture. Test strips are manufactured in batch lots. There is invariably slight lot-to-lot variations in the chemistries applied to test strips due to the complexities of the chemistries involved. It is therefore necessary to calibrate all portable blood glucose monitoring meters in use today to account for such lot-to-lot variations to assure consistent and accurate relationships between the color or resistance changes in such chemistries as measured by the meters and the corresponding blood glucose concentrations generated by the meter's microprocessor.

Lot-specific calibration factors for test strips are empirically derived by the test strip manufacturers. The lot specific calibration factors then accompany each package of test strips in a format that is suitable for use in a particular meter model. This has been accomplished to date in several different ways.

In one case, a bar code reader is provided in the meter. Lot-specific correction factors are provided with each package of test strips in a bar code format that can be read into the the meter's microprocessor through the meter's bar code reader. Another method requires that a lot-specific code number be entered into the meter's microprocessor using keys located on the meter. The code number calls up a particular correction curve that has been programmed into the meter's microprocessor. Yet another method provides an electronic module with each package of test strips that is inserted into a receiving socket on the meter. The module houses an electronic memory element that contains the lot-specific correcting information for the meter's microprocessor.

Whatever the precise method utilized to enter the lot-specific correction factors into the meter's microprocessor, the microprocessor applies the lot-specific correction factors to the measurements taken by the meter of the blood glucose-induced changes in test strip chemistry, and then generates a corrected digital readout of the patient's capillary blood glucose concentration in milligrams per milliliter. No known portable blood glucose monitoring meter in use today incorporates a man-readable, replaceable, lot-specific calibration means.

The drive to reduce the manufacturing costs of portable blood glucose monitoring meters led to a review of the foregoing methods of determining blood glucose concentrations. It was found that all portable blood glucose monitoring meters in use today have a common minimum manufacturing cost factor: the lower limit is determined by the cost of the microprocessor and the microprocessor-based electronic circuitry. Efforts to reduce the cost to patients of portable blood glucose monitoring meters are therefore impeded by the fixed costs of microprocessors and their related electronic circuitry.

The portable blood glucose monitoring meter of the present invention employs a different and less expensive approach to determine blood glucose concentrations from measurements taken of the blood glucose-induced changes in the chemistries of the disposable test strips of the prior art. The meter of the present invention provides a patient-operated device that incorporates calibration means to account for the lot-to-lot variation in test strip chemistries without the use of a microprocessor. The meter of the present invention therefore employs a more simple and less costly approach to determining blood glucose concentrations than is employed in any of the portable blood glucose monitoring meters in use today.

SUMMARY OF THE INVENTION

The portable blood glucose monitoring meter of the preferred embodiment of the invention employs an analog circuit in conjunction with a manually rotatable dial that varies the resistance of a potentiometer to locate a null position that balances the measure taken of the blood glucose-induced changes in the chemistries of disposable test strips. The dial supports a replaceable, pre-printed calibration disk. The calibration disk displays in man-readable format blood glucose concentrations in milligrams per milliliter that have been calibrated to the specific batch-lot chemistries of the disposable test strips used with the meter. A patient places a replaceable calibration disk upon the dial, and inserts a corresponding test strip bearing a drop of the patient's capillary blood into the meter. The patient then manually adjusts the dial until prompting arrows indicate a null position. If the dial has rotated past the null position, an opposing arrow will illuminate indicating a need to rotate the dial in the opposite direction. The procedure is repeated until a null position is found. At the null position, the prompting arrows illuminate simultaneously, or a third indicator is illuminated. The concentration of the patient's blood glucose in milligrams per milliliter is then read directly from the number appearing on the calibration disk at the null point. The concentration of blood glucose is interpolated in a manner similar to reading a common thermometer.

The basic principles of the portable blood glucose monitoring meter of the invention are well known. Early blood glucose measuring instruments utilized analog circuitry and were manufactured using the basic principles underlying the meter of the invention. However, the replaceable calibrated disk and the non-linear null prompting concepts of the present invention were not employed. The features of the portable blood glucose monitoring meter of the invention not found in the prior art include the ability to provide inexpensive means to calibrate test strip batch lots with a replaceable man-readable calibration disk, the non-linear null prompting system, and, the innovative circuitry that provides the novel reflectance system features without the use of a microprocessor. No portable blood glucose monitoring meter has heretofore utilized a manually operated dial that features a replaceable man-readable calibration disk with a non-linear null prompting system, as summarized.

Another embodiment of the present invention is, in a portable blood glucose monitoring meter having an analog circuit with a variable potentiometer to measure blood glucose-induced changes in the chemistries of disposable test strips to determine blood glucose concentrations, the improvement comprising: dial means to vary manually the resistance of the potentiometer to locate a null position that balances the measure of the blood glucose-induced changes in the chemistries of disposable test strips; calibration means integral with the dial means to receive replaceable, man-readable, pre-printed blood glucose concentrations that correspond to the null positions located by the dial means and that have been empirically calibrated to the batch lot variations in the chemistries of the disposable test strips used in the meter; and non-linear null prompting means to indicate the manual variation of the dial means required to achieve a null position.

Yet another another embodiment of the present invention is a method of determining blood glucose concentrations, comprising the steps of: providing a portable blood glucose monitoring meter having an analog circuit with a variable potentiometer to measure blood glucose-induced changes in the chemistries of disposable test strips to determine blood glucose concentrations, a manually replaceable dial to vary manually the resistance of the potentiometer to locate a null position that balances the measure of the blood glucose-induced changes in the chemistries of disposable test strips, calibration means integral with the dial to receive a man-readable, replaceable, pre-printed calibration disk containing blood glucose concentrations that correspond to the null positions located by the dial and that are empirically calibrated to the batch lot variations in the chemistries of the disposable test strips used in the meter, and non-linear null prompting means to indicate the manual variation of the dial means required to achieve a null position; positioning on the dial a replaceable, man-readable, pre-printed calibration disk containing blood glucose concentrations corresponding to the null positions located by the dial that are empirically calibrated to the chemistries of disposable test strips to be used in the meter; inserting a test strip bearing chemistry calibrated to the calibration disk and with a drop of capillary blood thereon into the meter; rotating the dial manually until the null prompting means indicates a null position; and reading directly from said calibration disk at the null point the concentration in milligrams per liter of blood glucose present in the drop of capillary blood upon the test strip.

It is an object of the present invention to provide a less costly portable blood glucose monitoring meter.

It is a further object of the present invention to provide a portable blood glucose monitoring meter that eliminates the need for costly microprocessor and microprocessor-based electronic circuitry thereby providing the means to lower the cost of portable blood glucose monitoring meters according to the invention.

It is a further object of the present invention to provide a portable blood glucose monitoring meter without a microprocessor or microprocessor-based electronic circuitry to incorporate lot-specific correction factors for disposable test strips.

It is a further object of the invention to provide a portable blood glucose monitoring meter with a non-linear null prompting system to locate a null position.

It is a further object of the invention to provide a portable blood glucose monitoring meter with temperature-based current compensation for the light emitting diode used in the reflectance measuring system utilized in the meter of the invention that does not require a microprocessor.

Related objects and advantages of the portable blood glucose monitoring meter of the present invention will be evident from the following description.

BRIEF DESCRIPTION OF THE DRAWINGS

FIG. 1 is a top plan view of one embodiment of the portable blood glucose monitoring meter of the invention.

FIG. 2 is a right side view of the portable blood glucose monitoring meter of FIG. 1.

FIG. 3 is a front elevational view of the portable blood glucose monitoring meter of FIG. 1.

FIG. 4 is a top plan view of one embodiment of the replaceable calibration disk utilized in the portable blood glucose monitoring meter of FIG. 1.

FIG. 5 is a top plan view of another embodiment of the replaceable calibration disk utilized in the portable blood glucose monitoring meter of FIG. 1.

DESCRIPTION OF THE PREFERRED EMBODIMENTS

Figure 6:
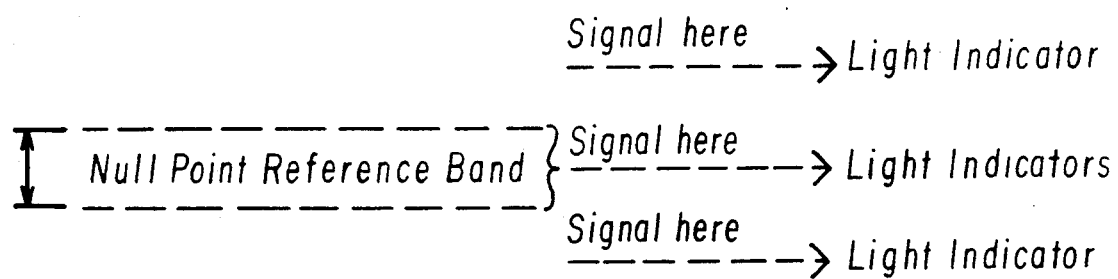
FIG. 6 is a diagram illustrating the operation of the non-linear null prompting system of the portable blood glucose monitoring meter of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Referring now to the drawings, there is shown in FIGS. 1-8 a preferred embodiment of the portable blood glucose monitoring meter 10 of the invention. Meter 10 employs an analog circuit in conjunction with a manually rotatable dial 12, rotated by adjustment knob 12a, to vary the resistance of a potentiometer to balance the measure of the blood glucose induced changes in the chemistries of the disposable test strips to be utilized in the meter 10. Dial 12 receives and supports a replaceable, pre-printed calibration disk 14 (FIG. 4). On the face of disk 14 are blood glucose concentration numbers in milligrams per milliliter of blood in a man-readable format. The numbers are calibrated, by their positioning about the periphery of disk 14, by empirical data to correspond to the specific batch lot variations in the chemistries of the disposable test strips to be used with the meter. A calibrated disk, such as disk 14 of FIG. 4, or disk 14' of FIG. 5, is created by the test strip manufacturer for each batch lot of test strips manufactured by testing the disposable test strips from each batch lot with a meter 10 to locate null positions at reference blood glucose concentrations. An exact duplicate of disk 14 (or 14') is then included in each package of test strips sold from the batch lot.

When a patient first opens a new package of disposable test strips, the calibration disk 14 accompanying the package would be removably affixed to dial 12 by a surface adhesive or the like. The face of meter 10 of FIG. 1 opens above dial 12 to allow access to the full face of circular dial 12 of the preferred embodiment to place disk 14 in a pre-registered orientation upon the face of dial 12 and/or to remove a prior calibration disk 14 from a previous package of test strips. The patient would then apply a drop of capillary blood to the chemistry of a test strip corresponding to the calibration disk 14, and insert the test strip bearing the blood into meter 10 at test strip inlet 18.

The patient then rotates dial 12, until the prompting arrows 20 and 22 indicate a null position. If the dial 12 has rotated past the null position, the opposing arrow 20 or 22 will illuminate indicating a need to rotate the dial 12 in the opposite direction. The procedure is repeated until a null position is found. At the null position, a third indicator may be incorporated (not shown) to indicate that the null position has been reached. Alternatively, the two prompting arrows 20 and 22 may illuminate simultaneously, as would be the case in the preferred embodiment shown in FIG. 1, as an indication that a null position has been reached, thus eliminating the need for a third indicator. The indicator arrows 20 and 22 may be light emitting diodes, liquid crystal display icons, incandescent lamps, or other means such as electromagnetic indicators.

The concentration of blood glucose within the patient's capillary blood may be read directly from the disk 12 when dial 12 has been rotated to a null position. In FIG. 1, if the position of the dial 12 as shown represented a null position, the patient would directly read a blood glucose concentration of 110 milligrams per milliliter.

The basic principles behind the meter 10 are well known. Early blood glucose measuring instruments, albeit table model versions, were manufactured using the basic analog circuit principles of meter 10 of the preferred embodiment. Lacking in those early blood glucose measuring instruments, and in any instruments thereafter, however, were the inexpensive means to calibrate test strip batch lot chemistry variations according to the present invention, such as calibration disk 14; the non-linear null prompting system of the present invention, as described; and the innovative circuitry to be described below that provides the non-linear null prompting system and other systems of the invention to be described below without the aid of a microprocessor.

Meter 10 of the preferred embodiment utilizes the disposable test strips of the prior art that are provided with chemistries that produce a color change in proportion to the concentration of blood glucose within capillary blood applied to the chemistry. Meter 10 of the preferred embodiment is therefore provided with known optical reflectance circuitry to measure the blood glucose-induced color changes in the chemistries on the disposable test strips, and to generate a signal against which the circuit is balanced by means of the potentiometer varied with dial 12. Meter 10 could also be equipped with known circuitry to measure the change in electrical resistance of the disposable test strips of the prior art that have chemistries that change electrical resistance in proportion to the concentration of blood glucose in blood applied thereto.

Figure 7:
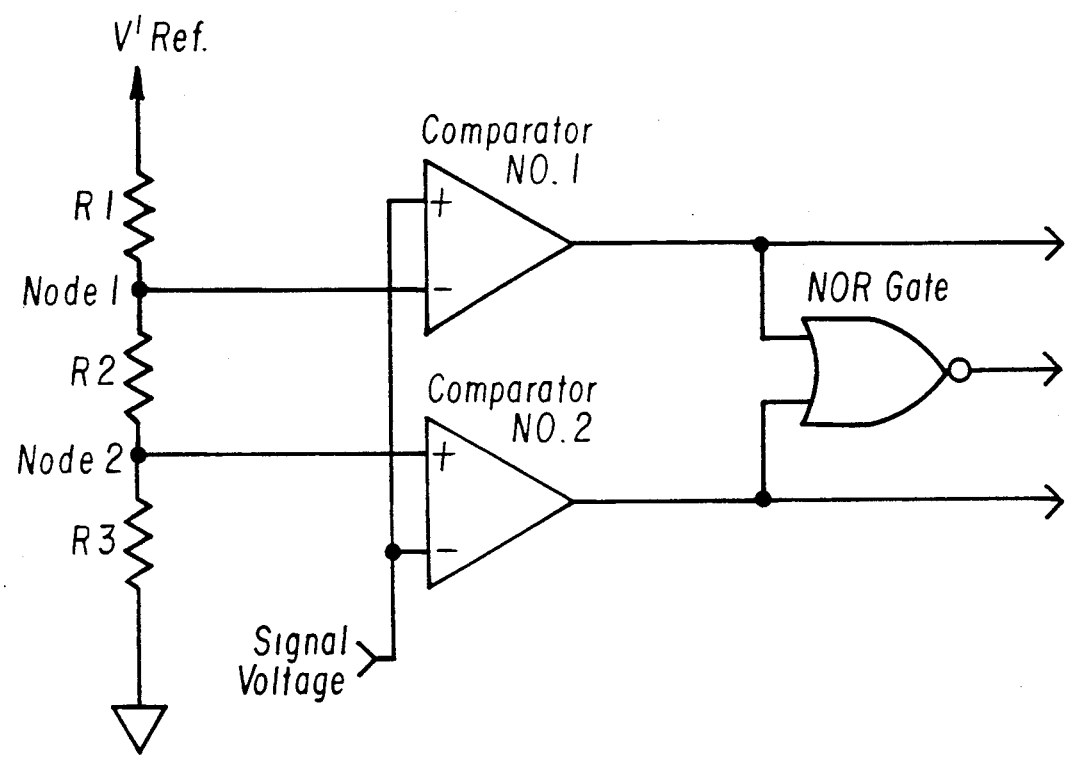
FIG. 7 is a circuit diagram showing the essential components of the non-linear null prompting system according to the invention.

Referring now to FIGS. 6 and 7, the null prompting system of the preferred embodiment provides up to three null prompting signals for use in meter 10 of the preferred embodiment. The three signals can be used in conjunction with indicator lights, such as the light emitting diodes that are indicating arrows 20 and 22 (FIG. 1) of the preferred embodiment, or the signals can be further modified, conventionally, for use with a liquid crystal display. The null prompting system of the preferred embodiment allows the patient to trigger an indicator, such as arrows 20 and 22, when the calibration dial is high of the null position, lower than the null position, or within a given reference band representing the null position (FIG. 6). The use of such a non-linear null prompting system allows the patient to improve the resolution of the meter 10 at the high glucose concentration end of the calibration disk 14.

FIG. 7 is a circuit diagram showing the essential components the non-linear null prompting system of the invention. Three resistors $R_1$, $R_2$, and $R_3$ are used. One resistor, $R_1$, is variable. Two voltage levels are derived from the resistor string. The Reference Voltage, $V'_{ref}$, at Node 1 is compared with a Signal Voltage using Comparator #1. The Reference Voltage at Node 2 is compared with the same Signal Voltage using Comparator #2. If the Reference Voltage at Node 1 is less that the Signal Voltage, then Comparator #1 outputs a high signal. This indicates that the null position reference band is below the Signal Voltage level. Comparator #2 outputs a high signal if the Reference Voltage at node 2 is greater than the Signal Voltage. This indicates that the null position reference band is above the Signal Voltage level. The outputs of comparator #1 and comparator #2 are input into a NOR gate, which is high if the Signal Voltage is both less than the Reference Voltage at Node 1 and greater than the Reference Voltage at node 2. This indicates that the Signal Voltage is within the reference band and that a null position has been reached.

Figure 8:
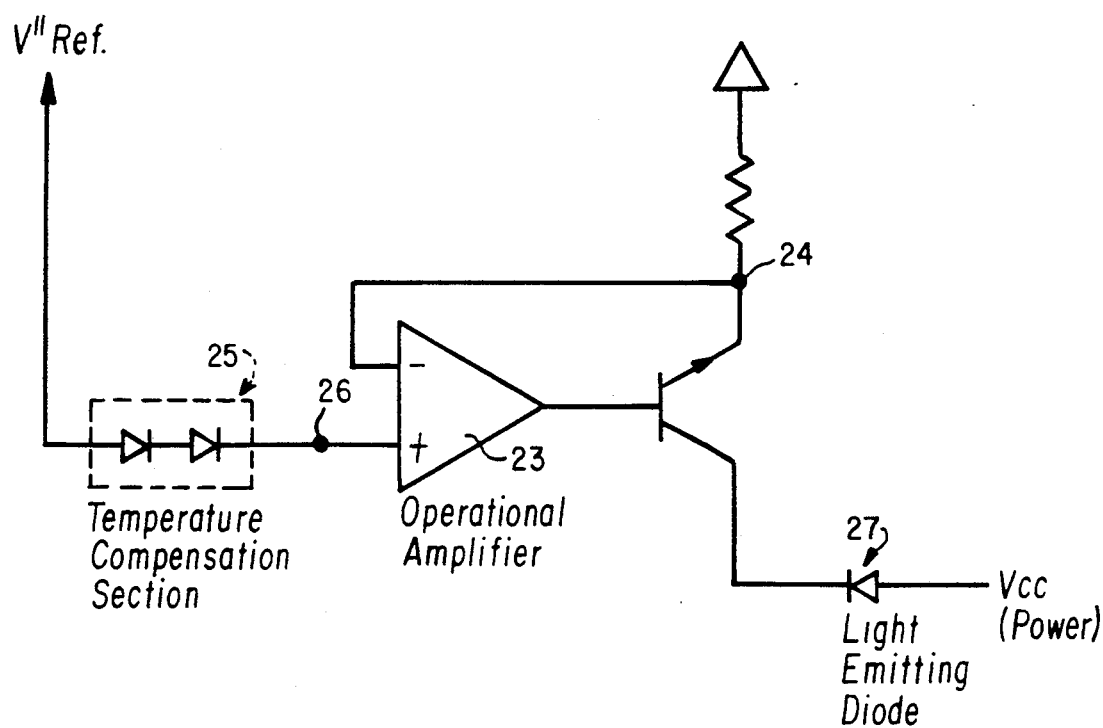
FIG. 8 is a circuit diagram showing the essential components of the temperature compensation scheme according to the invention.

The light source of the analog electronics used for the reflectance measuring system utilized in the preferred embodiment of meter 10 is a light emitting diode (27 in FIG. 8). Heretofore, the change in light emitting diode brightness with temperature in reflectance measuring systems has required compensation by scaling with a known color standard and calculations with a microprocessor. The temperature compensation scheme for the light emitting diode (27) of the reflectance measuring system of meter 10 uses diodes in conjunction with an amplifier and a reference voltage to achieve a constant light emitting diode (27) brightness for the reflectance measuring system even when the temperature is not constant. By selecting the number and type of diodes, and the reference voltage, one can compensate for the decrease in brightness when the temperature increases for a variety of different light emitting diodes. Diodes have been used for temperature compensation in a variety of circuits, however, they have not been used in a portable instrument such as meter 10 that uses a light emitting diode (27) as the light source for a reflectance measuring system.

FIGS. 8 illustrates the temperature compensation scheme of the preferred embodiment. The feedback of an operational amplifier 23 causes the voltage at point 24 to be equal to the voltage at point 26. This voltage is equal to the Reference Voltage, $V''_{ref}$, minus the voltage drop across the Temperature Compensation Section 25, which may consist of one or more diodes in series. In general, the brightness of a light emitting diode 27 decreases with increasing temperature. The Temperature Compensation Section's voltage drop must therefore decrease with increasing temperature. This causes the voltage at point 24 to increase with increasing temperature, which compensates for the loss in brightness of a light emitting diode 27 by supplying the light emitting diode with more current.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. In a portable blood glucose monitoring meter having an analog circuit with a variable potentiometer to measure blood glucose-induced changes in the chemistries of disposable test strips to determine blood glucose concentrations, the improvements comprising:

dial means to vary manually the resistance of said potentiometer to locate a null position that balances the measure of the blood glucose-induced changes in the chemistries of disposable test strips;

calibration means integral with said dial means to receive replaceable, pre-printed, man-readable blood glucose concentrations that correspond to the null positions located by said dial means and that are empirically calibrated to the batch lot variations in the chemistries of the disposable test strips used in the meter; and null prompting means to indicate the manual variation of said dial means required to achieve a null position.

2. The portable blood glucose monitoring meter of claim 1 wherein said dial means includes a manually rotatable dial.

3. The portable blood glucose monitoring meter of claim 2 wherein said manually rotatable dial supports a replaceable, man-readable, pre-printed calibration disk.

4. The portable blood glucose monitoring meter of claim 3 wherein said calibration disk displays man-readable blood glucose concentrations in milligrams per milliliter about its periphery that are calibrated by their position about the periphery to the specific batch-lot chemistries applied to the disposable test strips to be used with the meter.

5. The portable blood glucose monitoring meter of claim 1 wherein said null prompting means is non-linear and includes display means that indicate the direction of manual variation of said potentiometer required to locate a null position.

6. The portable blood glucose monitoring meter of claim 5 wherein said display means includes at least two illuminating indicators.

7. The portable blood glucose monitoring meter of claim 6 wherein said display means includes a pair of opposing illuminating arrows that individually illuminate when manual variation of the dial means in the direction indicated by the illuminated arrow is required to locate a null position.

8. The portable blood glucose monitoring meter of claim 7 wherein said illuminating means includes a pair of opposing illuminating arrows that illuminate simultaneously when a null position has been located.

9. The portable blood glucose monitoring meter of claim 1 further comprising at least one light emitting diode with temperature compensation means to achieve constant light emitting diode brightness as temperature varies in the absence of a microprocessor.

10. In a portable reflectance meter having an analog circuit with a potentiometer, the meter providing a measurement of color variances resulting from test solutions deposited on disposable chemically treated test strips to determine chemical concentrations of certain chemicals contained in the test solutions, the improvements comprising:

dial means for manually varying the resistance of said potentiometer to locate a null position that balances color changes of the disposable test strips against a reference;

calibration means integral with said dial means to receive replaceable, pre-printed, man-readable chemical concentration disks that correspond with the null position located by said dial means and that are empirically calibrated to correspond with the chemical characteristics of a particular batch of the disposable test strips used in the meter;

a light emitting diode for illuminating the chemically treated test strips;

first circuit means connected to said light emitting diode for providing a current signal to said light emitting diode, said current signal varying in accordance with variations in ambient temperature to maintain a constant intensity brightness signal from said light emitting diode; and null prompting means for indicating to the user the manual variation of said dial means required to achieve a null position.

11. The meter of claim 10 wherein said first circuit means includes means for detecting a change in ambient temperature and producing a temperature signal in response thereto, and amplifier means responsive to said temperature signal for producing said current signal in accordance with said temperature signal.

12. The meter of claim 11 wherein said means for detecting a change in ambient temperature is a diode.

13. The meter of claim 12 wherein said amplifier means includes an operational amplifier and wherein said diode is forward biased with the cathode of said diode connected to an input of said operational amplifier, said amplifier means further including a transistor, said transistor connected in a feedback loop with said operational amplifier with the base of said transistor connected to the output of said operational amplifier, and wherein said transistor produces said current signal.

14. A device for providing a constant brightness light signal comprising:

temperature compensation means for producing a temperature signal wherein said temperature compensation means is a diode and said temperature signal is the forward voltage drop across said diode;

power source means responsive to said temperature signal for producing a power signal in accordance with said temperature signal wherein said power source means includes an operational amplifier and a transistor wherein the diode is forward biased with the cathode of the diode connected to an input of the operational amplifier, wherein said transistor is connected in a feedback loop with said operational amplifier with the base of the transistor connected to the output of said operational amplifier, and wherein the transistor produces the power signal; and a light emitting diode responsive to said power signal and producing a constant intensity light signal in response thereto.

* * * * *

UNITED STATES PATENT AND TRADEMARK OFFICE
CERTIFICATE OF CORRECTION

PATENT NO.    : 5,174,963

DATED         : December 29, 1992

INVENTOR(S)   : Maurice D. Fuller et al.

It is certified that error appears in the above-identified patent and that said Letters Patent is hereby corrected as shown below:

In column 6, line 8, please change "110" to -- 130 --.

In column 6, line 22, please change "systems" to -- features --.

Signed and Sealed this

Nineteenth Day of October, 1993

Attest:

BRUCE LEHMAN

Attesting Officer     Commissioner of Patents and Trademarks